(12) United States Patent
Kimura et al.

(10) Patent No.: US 11,651,789 B2
(45) Date of Patent: May 16, 2023

(54) FLUOROPOLYETHER COMPOUND, LUBRICANT USING SAME AND USAGE THEREOF

(71) Applicant: Moresco Corporation, Kobe (JP)

(72) Inventors: Akinori Kimura, Kobe (JP); Tsuyoshi Shimizu, Kobe (JP)

(73) Assignee: MORESCO CORPORATION, Hyogo (JP)

( * ) Notice: Subject to any disclaimer, the term of this patent is extended or adjusted under 35 U.S.C. 154(b) by 23 days.

(21) Appl. No.: 17/424,741

(22) PCT Filed: Jan. 9, 2020

(86) PCT No.: PCT/JP2020/000473
§ 371 (c)(1),
(2) Date: Jul. 21, 2021

(87) PCT Pub. No.: WO2020/153139
PCT Pub. Date: Jul. 30, 2020

(65) Prior Publication Data
US 2022/0093127 A1      Mar. 24, 2022

(30) Foreign Application Priority Data

Jan. 24, 2019   (JP) .............................. JP2019-010447

(51) Int. Cl.
| | | |
|---|---|---|
| *G11B 5/725* | (2006.01) | |
| *C08G 65/00* | (2006.01) | |
| *C10M 107/38* | (2006.01) | |
| *G11B 5/667* | (2006.01) | |
| *C10N 40/00* | (2006.01) | |

(52) U.S. Cl.
CPC .......... *G11B 5/7257* (2020.08); *C08G 65/007* (2013.01); *C10M 107/38* (2013.01); *G11B 5/667* (2013.01); *C10M 2213/04* (2013.01); *C10M 2213/06* (2013.01); *C10N 2040/00* (2013.01)

(58) Field of Classification Search
None
See application file for complete search history.

(56) References Cited

U.S. PATENT DOCUMENTS

| | | |
|---|---|---|
| 2006/0052262 A1 | 3/2006 | Akada et al. |
| 2010/0160576 A1* | 6/2010 | Adcock ................... C07C 41/48 |
| | | 525/473 |
| 2010/0239887 A1 | 9/2010 | Kobayashi |
| 2014/0147699 A1 | 5/2014 | Kobayashi |
| 2017/0152456 A1 | 6/2017 | Sagata et al. |
| 2017/0260472 A1 | 9/2017 | Sagata et al. |
| 2019/0352573 A1 | 11/2019 | Hatta et al. |
| 2020/0283392 A1* | 9/2020 | Kato ..................... C07D 333/16 |
| 2022/0049176 A1* | 2/2022 | Yagyu .................. C08G 65/331 |

FOREIGN PATENT DOCUMENTS

| | | | |
|---|---|---|---|
| WO | 2004031261 A1 | 4/2004 | |
| WO | 2009066784 A1 | 5/2009 | |
| WO | 2015199037 A1 | 12/2015 | |
| WO | 2016084781 A1 | 6/2016 | |
| WO | 2018147017 A1 | 8/2018 | |
| WO | WO-2018139058 A1 * | 8/2018 | ......... C07C 43/1786 |

OTHER PUBLICATIONS

Kudyakova, Y.S., et al., "Perfluoroalkylation of Unsaturated Compounds in the Presence of Copper(II) Salen Complexes," Russian Journal of Organic Chemistry, 49(3): 469-471 (2013).

Bazhin, D.N., et al., "A Study of the Physico-Chemical Features of the [(Perfluoroalkyl)methyl]oxirane Amino Derivatives Based on the Hexafluoropropylene Oxide Trimer," Russian Journal of General Chemistry, 81(9):1829-1833 (2011).

International Search Report from corresponding PCT Application No. PCT/JP2020/000473 dated Mar. 31, 2020.

International Preliminary Report on Patentability from corresponding PCT Application No. PCT/JP2020/000473 dated Aug. 5, 2021.

* cited by examiner

*Primary Examiner* — Kevin M Bernatz
(74) *Attorney, Agent, or Firm* — Harness Dickey & Pierce P.L.C.

(57) ABSTRACT

An object of an aspect of the present invention is to provide: a lubricant excellent in adsorbability on the surface of a magnetic disk and in contamination resistance; and a magnetic disk which uses the lubricant and which is excellent in durability. The lubricant in accordance with an aspect of the present invention contains a fluoropolyether compound having, at a terminal thereof, a hydroxyalkenyl group or a hydroxyalkynyl group.

15 Claims, 1 Drawing Sheet

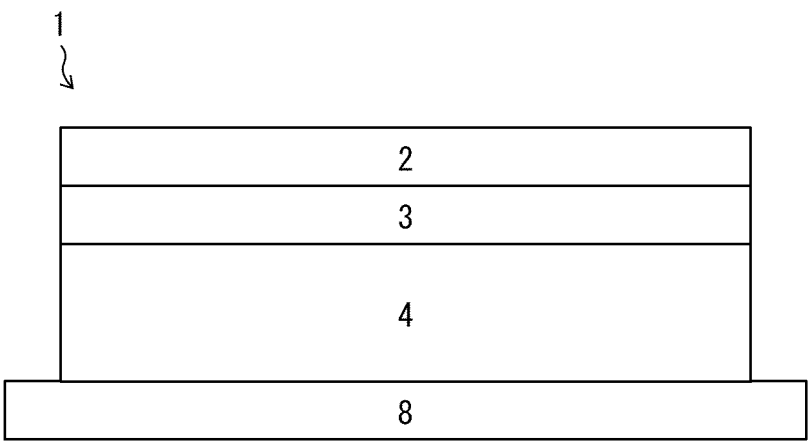
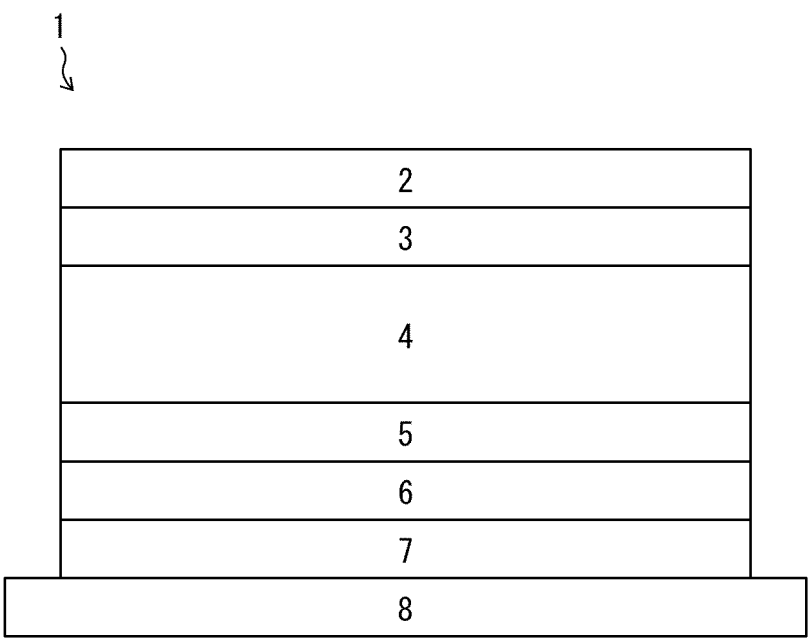

FLUOROPOLYETHER COMPOUND, LUBRICANT USING SAME AND USAGE THEREOF

PRIORITY STATEMENT

This application is a national stage application under 35 U.S.C. § 371 of PCT International Application No. PCT/JP2020/000473, which has an international filing date of 9 Jan. 2020 and claims priority under 35 U.S.C. § 119 to Japanese Patent Application No. 2019-010447 filed on 24 Jan. 2019. The contents of each application recited above are incorporated herein by reference in their entirety.

TECHNICAL FIELD

The present invention relates to a fluoropolyether compound, a lubricant containing the fluoropolyether compound, and usage thereof.

BACKGROUND ART

Many of the existing magnetic disks are constituted by: a recording layer disposed on a substrate; a protective layer disposed on the recording layer in order to protect information recorded on the recording layer; and a lubricant layer disposed on the protective layer.

With the increasing recording density of magnetic disks in recent years, the distance between a magnetic head and the surface of a magnetic disk has decreased to the order of ten nanometers so that information can be read from very small recording magnetic domains. Therefore, a lubricant for use in the lubricant layer is required to have long-term stability, chemical resistance, and the like characteristics even after formed into a thin film.

For example, Patent Document 1 discloses a lubricant including: a compound (A) which has a polar group, such as a hydroxyl group, a carboxyl group, an amino group, or an ester group, at both terminals of a perfluoropolyether having a specific main chain structure; and a compound (B) which has an apolar group at at least one terminal of a perfluoroether having the same main chain structure as the compound (A).

CITATION LIST

Patent Literature

[Patent Literature 1]
International Publication No. WO 2009/066784

SUMMARY OF INVENTION

Technical Problem

However, there is still room for improvement in order to obtain a lubricant excellent in adsorbability on the surface of a magnetic disk and in contamination resistance.

An object of an aspect of the present invention is to provide a lubricant excellent in adsorbability on the surface of a magnetic disk and in contamination resistance. An object of another aspect of the present invention is to provide a magnetic disk which uses the lubricant and which is excellent in durability.

Solution to Problem

The inventors of the present invention studied hard to attain the above objects, and found that it is possible to provide a lubricant excellent in adsorbability on the surface of a magnetic disk and in contamination resistance by using a fluoropolyether compound that has, at a terminal thereof, a hydroxyalkenyl group or a hydroxyalkynyl group. On the basis of this finding, the inventors accomplished the present invention. Specifically, the present invention includes the following arrangements.

An embodiment of the present invention is a fluoropolyether compound having a structure represented by Formula (1) below:

where:
$R^2$ represents a perfluoropolyether;
$R^1$ and $R^3$ each independently represent an organic group having, at a terminal thereof, a hydroxyl group, a halogenated alkyl group, an alkoxy group, a carboxy group, an amino group, an ester group, an amide group, or an aryl group; and
at least one of $R^1$ and $R^3$ contains a hydroxyalkenyl group which has a hydroxyl group at a terminal thereof, or a hydroxyalkynyl group which has a hydroxyl group at a terminal thereof.

Advantageous Effects of Invention

An aspect of the present invention makes it possible to provide a lubricant excellent in adsorbability on the surface of a magnetic disk and in contamination resistance. Another aspect of the present invention makes it possible to provide a magnetic disk which uses the lubricant and which is excellent in durability.

BRIEF DESCRIPTION OF DRAWINGS

FIG. 1 shows cross-sectional views illustrating structures of magnetic disks in accordance with embodiments of the present invention.

DESCRIPTION OF EMBODIMENTS

The following description will discuss embodiments of the present invention in detail. Note, however, that the present invention is not limited to the following embodiments, but can be altered within this disclosure. The present invention also encompasses, in its technical scope, any embodiment derived by combining technical means disclosed in differing embodiments. Note that the expression "A to B", representing a numerical range, herein means "not less than A and not more than B" unless otherwise specified in this specification.

(I) Fluoropolyether Compound

A fluoropolyether compound in accordance with an embodiment of the present invention (hereinafter, also referred to simply as "fluoropolyether compound") has a structure represented by Formula (1) below:

where:
$R^2$ represents a perfluoropolyether;
$R^1$ and $R^3$ each independently represent an organic group having, at a terminal thereof, a hydroxyl group, a halogenated alkyl group, an alkoxy group, a carboxy group, an amino group, an ester group, an amide group, or an aryl group; and at least one of $R^1$ and $R^3$ contains a hydroxyalkenyl group which has a hydroxyl group at a terminal thereof, or a hydroxyalkynyl group which has a hydroxyl group at a terminal thereof.

In the fluoropolyether compound in accordance with an embodiment of the present invention, one of $R^1$ and $R^3$ has a hydroxyalkenyl group or a hydroxyalkynyl group. That is, the fluoropolyether compound has at least one carbon-carbon double bond or at least one carbon-carbon triple bond. In a case where a functional group of a protective layer is covered with π electrons, which are electrons of a π bond constituting the carbon-carbon double bond or the carbon-carbon triple bond, one molecule can cover a plurality of functional groups of the protective layer. It is considered that this consequently makes the lubricant, which contains the fluoropolyether in accordance with an embodiment of the present invention, excellent in adsorbability on the surface of a magnetic disk and in contamination resistance. Therefore, the term "excellent in adsorbability on the surface of a magnetic disk" can be rephrased as "excellent in adsorbability on a protective layer at the surface of a magnetic disk".

In the present specification, whether or not a lubricant is "excellent in adsorbability on the surface of a magnetic disk" can be determined by carrying out a bonding ratio test described in Examples. In the present specification, whether or not a lubricant is "excellent in contamination resistance" can be determined by carrying out siloxane resistance evaluation described in Examples. The siloxane resistance evaluation is evaluation of how easily impurities attach to a protective layer, by measuring the amount of attached siloxane which is a typical contaminant in a production process of a magnetic disk.

In the fluoropolyether compound in accordance with an embodiment of the present invention, it is more preferable that each of both of $R^1$ and $R^3$ contain a hydroxyalkenyl group which has a hydroxyl group at a terminal thereof, or a hydroxyalkynyl group which has a hydroxyl group at a terminal thereof. In a case where $R^1$ and $R^3$ are arranged as above, it is possible to obtain a lubricant excellent in adsorbability on the surface of a magnetic disk and in contamination resistance.

In a case where at least one of $R^1$ and $R^3$ contains the hydroxyalkenyl group which has a hydroxyl group at a terminal thereof, it is preferable that the hydroxyalkenyl group have a structure represented by Formula (2) below. In a case where at least one of $R^1$ and $R^3$ contains the hydroxyalkynyl group which has a hydroxyl group at a terminal thereof, it is preferable that the hydroxyalkynyl group have a structure represented by Formula (3) below.

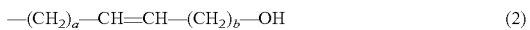

—(CH$_2$)$_a$—CH=CH—(CH$_2$)$_b$—OH　　(2)

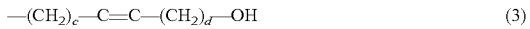

—(CH$_2$)$_c$—C≡C—(CH$_2$)$_d$—OH　　(3)

In Formula (2), a and b are each a real number of 1 to 4.
In Formula (3), c and d are each a real number of 1 to 4.
It is preferable that $R^2$ have a structure represented by Formula (4) below:

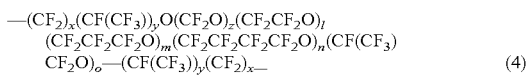

—(CF$_2$)$_x$(CF(CF$_3$))$_y$O(CF$_2$O)$_z$(CF$_2$CF$_2$O)$_l$
(CF$_2$CF$_2$CF$_2$O)$_m$(CF$_2$CF$_2$CF$_2$CF$_2$O)$_n$(CF(CF$_3$)
CF$_2$O)$_o$—(CF(CF$_3$))$_y$(CF$_2$)$_x$—　　(4)

where x is a real number of 0 to 3, y is a real number of 0 to 1, and z, l, m, n, and o are each a real number of 0 to 15.

In a case where at least one of $R^1$ and $R^3$ contains the hydroxyalkenyl group which has a hydroxyl group at a terminal thereof, it is preferable that the at least one of $R^1$ and $R^3$ have a structure represented by Formula (5) below. In a case where at least one of $R^1$ and $R^3$ contains the hydroxyalkynyl group which has a hydroxyl group at a terminal thereof, it is preferable that the at least one of $R^1$ and $R^3$ have a structure represented by Formula (6) below.

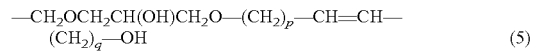

—CH$_2$OCH$_2$CH(OH)CH$_2$O—(CH$_2$)$_p$—CH=CH—
(CH$_2$)$_q$—OH　　(5)

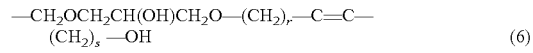

—CH$_2$OCH$_2$CH(OH)CH$_2$O—(CH$_2$)$_r$—C≡C—
(CH$_2$)$_s$—OH　　(6)

In Formula (5), p and q are each a real number of 1 to 4.
In Formula (6), r and s are each a real number of 1 to 4.
$R^3$ may have a structure represented by any one of Formulae (7) to (9) below.

—(CH$_2$CH(OH)CH$_2$O)$_t$—H　　(7)

—(CF$_2$)$_u$CF$_3$　　(8)

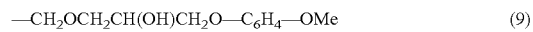

—CH$_2$OCH$_2$CH(OH)CH$_2$O—C$_6$H$_4$—OMe　　(9)

In Formula (7), t is a real number of 0 to 5.
In Formula (8), u is a real number of 0 to 3.
Further, an embodiment of the present invention encompasses a fluoropolyether compound having a structure represented by Formula (1') below.

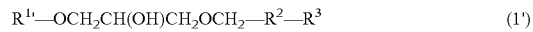

R$^{1'}$—OCH$_2$CH(OH)CH$_2$OCH$_2$—R$^2$—R$^3$　　(1')

In Formula (1'), $R^{1'}$ contains a hydroxyalkenyl group having a structure represented by Formula (2) below, or a hydroxyalkynyl group having a structure represented by Formula (3) below.

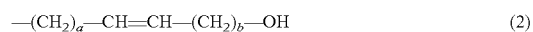

—(CH$_2$)$_a$—CH=CH—(CH$_2$)$_b$—OH　　(2)

—(CH$_2$)$_c$—C≡C—(CH$_2$)$_d$—OH　　(3)

In Formula (2), a and b are each a real number of 1 to 4.
In Formula (3), c and d are each a real number of 1 to 4.
$R^2$ has a structure represented by Formula (4) below:

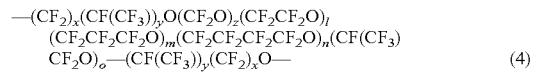

—(CF$_2$)$_x$(CF(CF$_3$))$_y$O(CF$_2$O)$_z$(CF$_2$CF$_2$O)$_l$
(CF$_2$CF$_2$CF$_2$O)$_m$(CF$_2$CF$_2$CF$_2$CF$_2$O)$_n$(CF(CF$_3$)
CF$_2$O)$_o$—(CF(CF$_3$))$_y$(CF$_2$)$_x$—　　(4)

where x is a real number of 0 to 3, y is a real number of 0 to 1, and z, l, m, n, and o are each a real number of 0 to 15.

$R^3$ contains a hydroxyalkenyl group having a structure represented by Formula (5) below, a hydroxyalkynyl group having a structure represented by Formula (6) below, or a structure represented by any of Formulae (7) to (9) below:

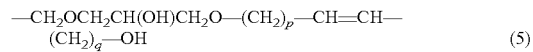

—CH$_2$OCH$_2$CH(OH)CH$_2$O—(CH$_2$)$_p$—CH=CH—
(CH$_2$)$_q$—OH　　(5)

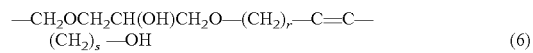

—CH$_2$OCH$_2$CH(OH)CH$_2$O—(CH$_2$)$_r$—C≡C—
(CH$_2$)$_s$—OH　　(6)

—(CH$_2$CH(OH)CH$_2$O)$_t$—H　　(7)

—(CF$_2$)$_u$CF$_3$　　(8)

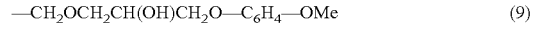

—CH$_2$OCH$_2$CH(OH)CH$_2$O—C$_6$H$_4$—OMe　　(9)

In Formula (5), p and q are each a real number of 1 to 4.
In Formula (6), r and s are each a real number of 1 to 4.
In Formula (7), t is a real number of 0 to 5.
In Formula (8), u is a real number of 0 to 3.
The fluoropolyether compound in accordance with an embodiment of the present invention is not limited to a particular kind and contains any combination of the foregoing $R^1$ to $R^3$, provided that the fluoropolyether compound is a compound represented by Formula (1) or (1') above. More specific examples of the fluoropolyether compound in accordance with an embodiment of the present invention include compounds each having a structure represented by any of Formulae below:

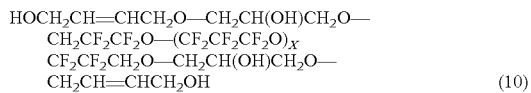  (10)

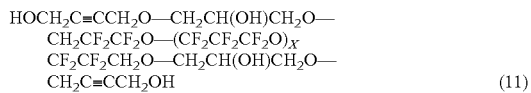  (11)

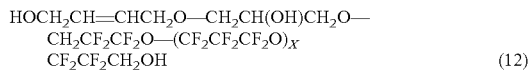  (12)

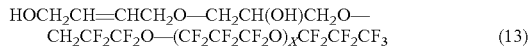  (13)

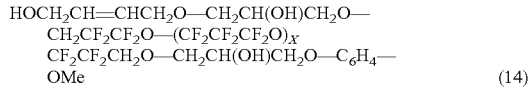  (14)

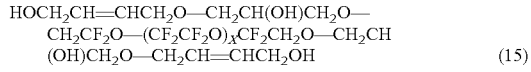  (15)

In Formulae (10) to (15) above, x is a real number of 1 to 15.

A method of producing a fluoropolyether compound in accordance with an embodiment of the present invention is not limited to a particular method. The fluoropolyether compound in accordance with an embodiment of the present invention can be obtained by reacting, for example, a linear fluoropolyether (a), which has a hydroxy group, with an alkene compound (A) or an alkyne compound (B), which has an epoxy group and a hydroxy group protected by a protective group.

When the linear fluoropolyether (a) having a hydroxy group is reacted with the alkene compound (A) or the alkyne compound (B) in the presence of a catalyst, the reaction temperature is 20° C. to 90° C., and preferably 60° C. to 80° C., and the reaction time is 5 hours to 20 hours, and preferably 10 hours to 18 hours. It is preferable to use 0.3 equivalents to 2.0 equivalents of the compound (A) or (B) and 0.05 equivalents to 0.5 equivalents of the catalyst, relative to the above compound (a). The catalyst can be an alkaline compound such as sodium t-butoxide and potassium t-butoxide. The reaction may be carried out in a solvent. Examples of the solvent include t-butyl alcohol, toluene, and xylene.

Thereafter, a resulting product is, for example, neutralized, washed with water, and purified by silica gel chromatography, so that an intended precursor is obtained. Subsequently, after deprotection through a hydrolysis reaction or the like of an ester group, a silyl group, or an alkoxy group, fractionation by column chromatography is carried out. As a result, it is possible to obtain an intended fluoropolyether compound as a fraction. The deprotection means an elimination reaction of the ester group, the silyl group or the alkoxy group.

The fluoropolyether (a) having a hydroxy group can be, for example, a compound having a structure represented by $HOCH_2CF_2CF_2O(CF_2CF_2CF_2O)_xCF_2CF_2CH_2OH$. This fluoropolyether has a number average molecular weight of 500 to 4000, and preferably 800 to 2000. The number average molecular weight here is a value determined by $^{19}F$-NMR using JNM-ECX400 available from JEOL Ltd. In NMR determination, a sample (fluoropolyether) was not diluted with a solvent, but directly used. A known peak of a part of the skeleton structure of the fluoropolyether is used as a reference of chemical shift. x is a real number of 1 to 35, and preferably a real number of 3 to 12. When x is a real number of 3 to 12, the molecular chain of the fluoropolyether becomes flatter. Thus, it is preferable that x be a real number of 3 to 12.

The fluoropolyether (a) is a compound having a molecular weight distribution. The molecular weight distribution (PD) of the fluoropolyether (a) is expressed as weight average molecular weight/number average molecular weight, and is 1.0 to 1.5, preferably 1.0 to 1.3, and more preferably 1.0 to 1.1. Note that the molecular weight distribution is a characteristic value obtained with use of HPLC-8220GPC available from Tosoh Corporation, a column (PLgel Mixed E) available from Polymer Laboratories, a HCFC-based CFC substitute as an eluent, and a non-functional perfluoropolyether as a reference substance.

There is no particular limitation on a method of synthesizing the alkene compound (A) or the alkyne compound (B), which has an epoxy group and a hydroxy group protected by a protective group.

For example, first, a mixture is obtained by mixing: an alkene compound or an alkyne compound, which has a hydroxy group at both terminals thereof; and a compound which reacts with the hydroxy group to form an ester group, a silyl group, or an alkoxy group. The mixture is stirred while heated. The reaction temperature is 10° C. to 60° C., and preferably 20° C. to 40° C. The reaction time is 2 hours to 20 hours, and preferably 10 hours to 18 hours. The compound which forms the ester group, the silyl group, or the alkoxy group is used preferably in an amount of 0.2 equivalents to 0.5 equivalents, relative to the alkene compound or the alkyne compound. It is possible use a reaction accelerator such as imidazole. Thereafter, for example, purification by silica gel column chromatography is carried out. It is possible to obtain, as a result, an alkene compound or an alkyne compound, which has a hydroxy group at one terminal thereof and an ester group, a silyl group, or an alkoxy group at the other terminal thereof.

The alkene compound having a hydroxy group at both terminals thereof is, for example, a compound having a structure represented by $HO-(CH_2)_p-CH=CH-(CH_2)_q-OH$ (where p and q are each a real number of 1 to 4). The alkyne compound having a hydroxy group at both terminals thereof is, for example, a compound having a structure represented by $HO-(CH_2)_r-C\equiv C-(CH_2)_s-OH$ (where r and s are each a real number of 1 to 4).

Examples of the compound which reacts with the hydroxy group to form an ester group, a silyl group, or an alkoxy group include an acid anhydride, a silyl halide, an alkyl halide, and an ether compound.

Examples of the acid anhydride includes a compound having a structure represented by $R^aOR^b$ ($R^a$ and $R^b$ are identical to or different from each other and each represents $CH_3CO$, $PhCO$, $CH_3SO_2$, $PhSO_2$, $CF_3CH_2CO$, and $CH_3C_6H_4SO_2$ (Ph represents a phenyl), a maleic anhydride, a succinic anhydride, and a phthalic anhydride. Specific examples of the acid anhydride include trifluoromethylacetic anhydride, benzoic anhydride, p-toluenesulfonic anhydride, trifluoromethanesulphonic anhydride, acetic anhydride, maleic anhydride, succinic anhydride, phthalic anhydride, acetic benzoic anhydride, methanesulphonic anhydride, and benzenesulfonic anhydride.

Examples of the silyl halide include a compound having a structure represented by $(R^c)_3SiY$, $R^d(R^e)_2SiY$, and $R^d R^e R^g SiY$ (in each of which: $R^c$ is $C_1$-$C_4$ alkyl or Ph; $R^d$ is $C_1$-$C_{18}$ alkyl, $C_1$-$C_4$ alkoxy, Ph, PhCH$_2$, pentafluorophenyl, cyanopropyl, or vinyl; $R^e$ is $C_1$-$C_2$ alkyl or Ph; and $R^g$ is $C_1$-$C_4$ alkyl which is replaced by a phenyl group). Specific examples of the silyl halide includes trimethyl silyl chloride, triethyl silyl chloride, triisopropyl silyl chloride, t-butyl dimethyl silyl chloride, t-butyl diphenyl silyl chloride, (3-cyanopropyl)dimethyl chlorosilane, benzyl chlorodimethyl silane, butyl dimethyl chlorosilane, chloro(decyl)dimethylsilane, chloro(dodecyl)dimethyl silane, chlorodimethyl (3-phenylpropyl)silane, chlorodimethyl phenyl silane, chlorodimethyl propyl silane, chlorodimethyl vinyl silane, diethyl isopropyl silyl chloride, dimethyl-n-octyl chlorosilane, dimethyl ethyl silyl chloride, dimethyl isopropyl chlorosilane, dimethyl octadecyl chlorosilane, diphenyl methyl chlorosilane, methyloctadecyl(3-phenylpropyl) chlorosilane, pentafluorophenyl dimethyl chlorosilane, t-butoxy diphenyl chlorosilane, t-butyl diphenyl chlorosilane, and triphenyl chlorosilane.

Examples of the alkyl halide include a compound represented by AY (where: A is $C_1$-$C_5$ alkyl; and Y is a halogen such as chlorine, bromine, or iodine). Specific examples of the alkyl halide include methyl halides, ethyl halides, propyl halides, butyl halides, and pentyl halides, such as iodomethane, 1-bromoethane, 2-bromopropane, 1-iodopropane, 2-iodopropane, 1-bromo-2-methylpropane, 1-bromobutane, 2-bromo-2-methylpropane, 2-bromobutane, 1-iodo-2-methylpropane, 1-iodobutane, 2-iodo-2-methylpropane, 2-iodobutane, 1-iodo-2-methylbutane, 1-iodo-3-methylbutane, 1-bromo-3-methylbutane, 1-bromopentane, 2-bromo-2-methylbutane, and 3-bromopentane.

Specific examples of the ether compound include chloromethylmethyl ether, 2-methoxyethoxymethyl chloride, benzyl chloromethyl ether, 3,4-dihydro-2H-pyran, and ethyl vinyl ether.

(II) Lubricant

A lubricant in accordance with an embodiment of the present invention is not limited to a particular kind, provided that the lubricant contains the fluoropolyether compound in accordance with an embodiment of the present invention.

With regard to the lubricant, the fluoropolyether compound in accordance with an embodiment of the present invention may be used alone as the lubricant. Alternatively, the fluoropolyether compound in accordance with an embodiment of the present invention and some other component mixed at a certain ratio may be used as the lubricant, provided that the performance of the fluoropolyether compound is not impaired.

Examples of the above-described other component include: known lubricants for magnetic disks, such as Fomblin (registered trademark) Zdol (available from Solvay Solexis), Ztetraol (available from Solvay Solexis), and Demnum (registered trademark) (available from Daikin Industries, Ltd.); and PHOSFAROL A20H (available from MORESCO Corporation).

(III) Magnetic Disk

A magnetic disk in accordance with an embodiment of the present invention includes, as illustrated in (a) of FIG. 1, a recording layer 4, a protective film layer (protective layer) 3, and a lubricant layer 2, which are disposed on a non-magnetic substrate 8. The magnetic disk can be any magnetic disk, provided that the lubricant layer 2 contains the foregoing lubricant.

In another embodiment, a magnetic disk can include, like a magnetic disk 1 illustrated in (b) of FIG. 1, a lower layer 5 that underlies the recording layer 4, one or more soft magnetic lower layers 6 that underlie the lower layer 5, and an adhesive layer 7 that underlies the one or more soft magnetic lower layers 6. In one embodiment, all of these layers can be formed on the non-magnetic substrate 8, which can contain glass. Each of the layers of the magnetic disk 1 other than the lubricant layer 2 can contain a material that is known in this technical field to be suitable for a corresponding layer of a magnetic disk.

(IV) Method of Producing Magnetic Disk

A method of producing a magnetic disk in accordance with an embodiment of the present invention includes the step of forming a lubricant layer by placing a lubricant in accordance with an embodiment of the present invention on the exposed surface of a protective layer of a stack of a recording layer and the protective layer.

There is no particular limitation on a method of forming a lubricant layer by placing the lubricant on the exposed surface of a protective layer of a stack of a recording layer and the protective layer.

It is preferable that the lubricant be placed on the exposed surface of the protective layer by the following method: the lubricant is diluted with a solvent and then placed on the exposed surface. Examples of the solvent include: PF-5060, PF-5080, HFE-7100, and HFE-7200 available from 3M; and Vertrel-XF (registered trademark) available from DuPont. The lubricant diluted with a solvent has a concentration of preferably 0.001 wt % to 1 wt %, more preferably 0.005 wt % to 0.5 wt %, and even more preferably 0.01 wt % to 0.1 wt %. When the concentration of the lubricant diluted with a solvent is 0.01 wt % to 0.1 wt %, the viscosity of the lubricant is low enough to easily control the thickness of the lubricant layer; thus, it is preferable that the concentration of the diluted lubricant be 0.01 wt % to 0.1 wt %.

The following arrangement may be employed: the recording layer and the protective layer are formed in this order; the lubricant is placed on the exposed surface of the protective layer; and then ultraviolet irradiation or heat treatment is carried out.

Carrying out ultraviolet irradiation or heat irradiation forms stronger bonds between the lubricant layer and the exposed surface of the protective layer and, in turn, prevents the lubricant from evaporating due to heating. Thus, it is preferable that ultraviolet irradiation or heat irradiation be carried out. When carrying out ultraviolet irradiation, it is preferable to use an ultraviolet ray having a wavelength of 185 nm or 254 nm as the dominant wavelength, in order to activate the exposed surface of the protective layer without affecting deep areas of the lubricant layer and the protective layer. The temperature of the heat treatment is preferably 60° C. to 170° C., more preferably 80° C. to 170° C., and even more preferably 80° C. to 150° C.

An embodiment of the present invention may be configured as in any of the following [1] to [9].

[1] A fluoropolyether compound having a structure represented by Formula (1) below:

$$R^1\text{—}R^2\text{—}R^3 \tag{1}$$

where:

$R^2$ represents a perfluoropolyether;

$R^1$ and $R^3$ each independently represent an organic group having, at a terminal thereof, a hydroxyl group, a halogenated alkyl group, an alkoxy group, a carboxy group, an amino group, an ester group, an amide group, or an aryl group; and at least one of $R^1$ and $R^3$ contains a hydroxyalkenyl group which has a hydroxyl group at a terminal thereof, or a hydroxyalkynyl group which has a hydroxyl group at a terminal thereof.

[2] The fluoropolyether compound as described in [1], wherein:

in a case where at least one of $R^1$ and $R^3$ contains the hydroxyalkenyl group which has a hydroxyl group at a terminal thereof, the hydroxyalkenyl group has a structure represented by Formula (2) below; and in a case where at least one of $R^1$ and $R^3$ contains the hydroxyalkynyl group which has a hydroxyl group at a terminal thereof, the hydroxyalkynyl group has a structure represented by Formula (3) below:

$$—(CH_2)_a—CH{=}CH—(CH_2)_b—OH \quad (2)$$

where a and b are each a real number of 1 to 4, and $$—(CH_2)_c—C{\equiv}C—(CH_2)_d—OH \quad (3)$$

where c and d are each a real number of 1 to 4.

[3] The fluoropolyether compound as described in [1] or [2], wherein $R^2$ has a structure represented by Formula (4) below:

$$\begin{aligned}—(CF_2)_x(CF(CF_3))_yO(CF_2O)_z(CF_2CF_2O)_l\\(CF_2CF_2CF_2O)_m(CF_2CF_2CF_2CF_2O)_n(CF(CF_3)\\CF_2O)_o—(CF(CF_3))_y(CF_2)_x—\end{aligned} \quad (4)$$

where
x is a real number of 0 to 3,
y is a real number of 0 to 1, and
z, l, m, n, and o are each a real number of 0 to 15.

[4] The fluoropolyether compound as described in any one of [1] to [3], wherein:

in a case where at least one of $R^1$ and $R^3$ contains the hydroxyalkenyl group which has a hydroxyl group at a terminal thereof, the at least one of $R^1$ and $R^3$ has a structure represented by Formula (5) below; and in a case where at least one of $R^1$ and $R^3$ contains the hydroxyalkynyl group which has a hydroxyl group at a terminal thereof, the at least one of $R^1$ and $R^3$ has a structure represented by Formula (6) below:

$$—CH_2OCH_2CH(OH)CH_2O—(CH_2)_p—CH{=}CH—(CH_2)_q—OH \quad (5)$$

where p and q are each a real number of 1 to 4, and $$—CH_2OCH_2CH(OH)CH_2O—(CH_2)_r—C{\equiv}C—(CH_2)_s—OH \quad (6)$$

where r and s are each a real number of 1 to 4.

[5] A fluoropolyether compound having a structure represented by Formula (1') below:

$$R^{1'}—OCH_2CH(OH)CH_2OCH_2—R^2—R^3 \quad (1')$$

where:
(i) $R^{1'}$ contain
a hydroxyalkenyl group having a structure represented by Formula (2) below, or
a hydroxyalkynyl group having a structure represented by Formula (3) below:

$$—(CH_2)_a—CH{=}CH—(CH_2)_b—OH \quad (2)$$

where a and b are each a real number of 1 to 4, or $$—(CH_2)_c—C{\equiv}C—(CH_2)_d—OH \quad (3)$$

where c and d are each a real number of 1 to 4;
(ii) $R^2$ has a structure represented by Formula (4) below:

$$\begin{aligned}—(CF_2)_x(CF(CF_3))_yO(CF_2O)_z(CF_2CF_2O)_l\\(CF_2CF_2CF_2O)_m(CF_2CF_2CF_2CF_2O)_n(CF(CF_3)\\CF_2O)_o—(CF(CF_3))_y(CF_2)_xO—\end{aligned} \quad (4)$$

where
x is a real number of 0 to 3,
y is a real number of 0 to 1, and
z, l, m, n, and o are each a real number of 0 to 15; and (iii) $R^3$ contains
a hydroxyalkenyl group having a structure represented by Formula (5) below,
a hydroxyalkynyl group having a structure represented by Formula (6) below, or
a structure represented by any of Formulae (7) to (9) below:

$$—CH_2OCH_2CH(OH)CH_2O—(CH_2)_p—CH{=}CH—(CH_2)_q—OH \quad (5)$$

$$—CH_2OCH_2CH(OH)CH_2O—(CH_2)_r—C{\equiv}C—(CH_2)_s—OH \quad (6)$$

$$—(CH_2CH(OH)CH_2O)_t—H \quad (7)$$

$$—(CF_2)_uCF_3 \quad (8)$$

$$—CH_2OCH_2CH(OH)CH_2O—C_6H_4—OMe \quad (9).$$

In Formula (5), p and q are each a real number of 1 to 4.
In Formula (6), r and s are each a real number of 1 to 4.
In Formula (7), t is a real number of 0 to 5.
In Formula (8), u is a real number of 0 to 3.

[6] A fluoropolyether compound having a structure represented by any of Formulae (10) to (15) below:

$$\begin{aligned}HOCH_2CH{=}CHCH_2O—CH_2CH(OH)CH_2O—\\CH_2CF_2CF_2O—(CF_2CF_2CF_2O)_X\\CF_2CF_2CH_2O—CH_2CH(OH)CH_2O—\\CH_2CH{=}CHCH_2OH\end{aligned} \quad (10)$$

$$\begin{aligned}HOCH_2C{\equiv}CCH_2O—CH_2CH(OH)CH_2O—\\CH_2CF_2CF_2O—(CF_2CF_2CF_2O)_X\\CF_2CF_2CH_2O—CH_2CH(OH)CH_2O—\\CH_2C{\equiv}CCH_2OH\end{aligned} \quad (11)$$

$$\begin{aligned}HOCH_2CH{=}CHCH_2O—CH_2CH(OH)CH_2O—\\CH_2CF_2CF_2O—(CF_2CF_2CF_2O)_X\\CF_2CF_2CH_2OH\end{aligned} \quad (12)$$

$$\begin{aligned}HOCH_2CH{=}CHCH_2O—CH_2CH(OH)CH_2O—\\CH_2CF_2CF_2O—(CF_2CF_2CF_2O)_XCF_2CF_2CF_3\end{aligned} \quad (13)$$

$$\begin{aligned}HOCH_2CH{=}CHCH_2O—CH_2CH(OH)CH_2O—\\CH_2CF_2CF_2O—(CF_2CF_2CF_2O)_X\\CF_2CF_2CH_2O—CH_2CH(OH)CH_2O—C_6H_4—\\OMe\end{aligned} \quad (14)$$

$$\begin{aligned}HOCH_2CH{=}CHCH_2O—CH_2CH(OH)CH_2O—\\CH_2CF_2O—(CF_2CF_2O)_XCF_2CH_2O—CH_2CH\\(OH)CH_2O—CH_2CH{=}CHCH_2OH\end{aligned} \quad (15)$$

wherein x is a real number of 1 to 15.

[7] A lubricant comprising a fluoropolyether compound described in any one of [1] to [6].

[8] A magnetic disk comprising: a recording layer; a protective layer disposed on the recording layer; and a lubricant layer disposed on the protective layer, the lubricant layer containing a lubricant described in [7].

[9] A method of producing a magnetic disk that includes a recording layer, a protective layer disposed on the recording layer, and a lubricant layer disposed on the protective layer, the method including the step of forming the lubricant layer by placing a lubricant recited in [7] on an exposed surface of the protective layer of a stack of the recording layer and the protective layer.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will more specifically discuss the present invention based on Examples; however, the present invention is not limited to the following Examples. In the following Examples, a bonding ratio test and siloxane resistance evaluation were carried out in the following manner.

(Bonding Ratio Test)

Compounds each synthesized as a lubricant by a method described later were each dissolved in Vertrel-XF (registered trademark) available from Dupont, at a certain concentration. Into a solution thus obtained, a magnetic disk of 2.5 inches in diameter was immersed for 5 minutes and pulled up at a speed of 2 mm/s from the solution. Note that the magnetic disk in the (Bonding ratio test) means a structure which includes a recording layer and a protective film layer (protective layer), which are disposed on a non-magnetic substrate. Thereafter, air drying was carried out for 10 minutes, and the thickness of respective films of the compounds thus applied was measured by FT-IR. The thickness of the films measured at this time is defined as a film thickness f. Next, the magnetic disks, to which the compounds had been applied, respectively, were each immersed in Vertrel-XF (registered trademark) for 5 minutes and then pulled up at 2 mm/s from the solution. Thereafter, air drying was carried out again for 10 minutes, and the thickness of respective films of the compounds thus applied was measured again by FT-IR. The film thickness measured at this time is defined as a film thickness b. The bonding rate is generally used as an index indicative of a degree of adsorbability on the surface of each of the magnetic disks. The bonding ratio is calculated by the following expression:

bonding ratio (%)=100×film thickness $b$/film thickness $f$ (Siloxane Resistance Evaluation)

A certain amount of each of Compounds 1 to 6 synthesized and of Compounds 7 to 11 of Comparative Examples was dissolved in Vertrel-XF (registered trademark) (150 g) available from DuPont, and stirring was carried out for 1 hours to prepare a lubricant solution. Then, Graphite powder <20 μm (1.0 g) available from Aldrich was added to the lubricant solution thus obtained, and then stirring was carried out for another 1 hour. Filtration was carried out with use of a membrane filter, so that graphite on which the lubricant was adsorbed was obtained. After the graphite on which the lubricant was adsorbed was dried at room temperature for 15 hours, the graphite (0.1 g) on which the lubricant was adsorbed was weighed on a Petri dish. The Petri dish containing the graphite on which the lubricant was adsorbed and a vial containing 0.5 g of octamethylcyclotetrasiloxane (hereinafter referred to as D4 in this specification) available from Tokyo Chemical Industry Co., Ltd. were placed in a container and hermetically closed. Then, the graphite on which the lubricant was adsorbed was exposed to D4 at room temperature (25° C.) for 24 hours. The Petri dish was taken out from the container and methanol (2.2 g) was added to the Petri dish, so that D4 attached to the graphite was extracted. Thereafter, filtration was carried out with use of a membrane filter, and a filtrate thus obtained was analyzed with use of a gas chromatograph (available from HEWLETT PACKARD, Product No. HP6890), so that the amount of D4 attached to the graphite was measured. The graphite on which the lubricant was adsorbed was heated to 550° C. with use of a thermogravimetric analyzer (available from EXTER, TG/DTA) in a nitrogen atmosphere at a temperature increase rate of 2° C./min. Then, the percentage of the lubricant that was adsorbed on the graphite, relative to the mass of the graphite, was determined.

Example 1

Compound 1 having a structure represented by Formula (10) below was synthesized as follows:

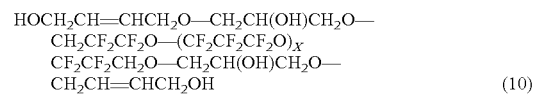

(10)

Into a flask, 100 g of (Z)-but-2-ene-1,4-diol, 100 g of DMF, and 74 g of imidazole were put and stirred. Further, into the flask, 173 g of triisopropyl silyl chloride was dropped while the flask was immersed in an ice bath. After dropping of triisopropyl silyl chloride was completed, stirring was carried out at room temperature for 15 hours. Thereafter, a resulting product was washed with water and purified by silica gel chromatography, so that 98 g of Compound 1a: (Z)-4-((triisopropylsilyl)oxy)but-2-en-1-ol was obtained. Into another flask, 60 g of Compound 1a, 51 g of t-butyl alcohol, 29 g of potassium-t-butoxide, and 460 g of epichlorohydrin were put and stirred in an argon atmosphere at 70° C. Then, a resulting product was purified by silica gel chromatography, so that 68 g of Compound 1b: (Z)-triisopropyl((4-(oxiran-2-ylmethoxy)but-2-ene-1-yl)oxy)silane was obtained.

Into another flask, 40 g of this compound 1b, 100 g of perfluoropolyether (number average molecular weight 1142) having a structure represented by HO—$CH_2CF_2CF_2O$—($CF_2CF_2CF_2O)_xCF_2CF_2CH_2$—OH, 42 g of t-butyl alcohol, and 8 g of potassium t-butoxide were put and stirred in an argon atmosphere at 70° C. for 17 hours. Then, 133 g of a brown liquid was obtained by neutralization and washing with water. Next, 80 g of the brown liquid and 80 g of SR solvent were put in another flask, and 126 g of 1 mol/L tetrahydrofuran solution of tetrabutylammonium fluoride was dropped into the flask. Then, stirring was carried out for 6 hours. Subsequently, 77 g of Compound 1, which was a colorless transparent liquid, was obtained by neutralization and purification by silica gel chromatography. The results of identification of Compound 1 by the NMR are as follows.

$^{19}$F-NMR (solvent: none, reference: OCF$_2$C$\underline{F}_2$CF$_2$O in the product [−129.7 ppm])

δ=−129.7 ppm, −129.6 ppm [14F, —OCF$_2$C$\underline{F}_2$CF$_2$O—]

δ=−123.9 ppm [4F, HOCH$_2$CH═CHCH$_2$O—CH$_2$CH(OH)CH$_2$O—CH$_2$C$\underline{F}_2$CF$_2$O—]

δ=−86.3 ppm [4F, HOCH$_2$CH═CHCH$_2$O—CH$_2$CH(OH)CH$_2$O—CH$_2$CF$_2$C$\underline{F}_2$O—]

δ=−84.0 ppm [28F, —OC$\underline{F}_2$CF$_2$C$\underline{F}_2$O—]

Results of $^{19}$F-NMR showed that for Compound 1, x=7.2.

1H-NMR (solvent: none, reference substance: D$_2$O)

δ=3.1 ppm to 4.5 ppm [26H, HOC$\underline{H}_2$CH═CHC$\underline{H}_2$O—C$\underline{H}_2$CH(OH)C$\underline{H}_2$O—C$\underline{H}_2$CF$_2$CF$_2$O—]

δ=5.0 ppm to 5.8 ppm [4H, HOCH$_2$C$\underline{H}$═C$\underline{H}$CH$_2$O—CH$_2$CH(OH)CH$_2$O—CH$_2$CF$_2$CF$_2$O—]

Example 2

Compound 2 having a structure represented by Formula (11) below was synthesized as follows:

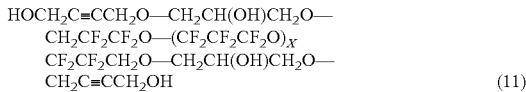

$$\begin{aligned}&\text{HOCH}_2\text{C}{\equiv}\text{CCH}_2\text{O}{-}\text{CH}_2\text{CH(OH)CH}_2\text{O}{-}\\&\text{CH}_2\text{CF}_2\text{CF}_2\text{O}{-}(\text{CF}_2\text{CF}_2\text{CF}_2\text{O})_x\\&\text{CF}_2\text{CF}_2\text{CH}_2\text{O}{-}\text{CH}_2\text{CH(OH)CH}_2\text{O}{-}\\&\text{CH}_2\text{C}{\equiv}\text{CCH}_2\text{OH}\end{aligned} \qquad (11)$$

Compound 2 (58 g) was obtained as in Example 1 except that 2-butyne-1,4-diol was used in place of (Z)-but-2-ene-1,4-diol. Compound 2 was a colorless transparent liquid. The results of identification of Compound 2 by the NMR are as follows.

$^{19}$F-NMR (solvent: none, reference: OCF$_2$C$\underline{F}_2$CF$_2$O in the product [−129.7 ppm])
δ=−129.7 ppm, −129.6 ppm [14F, —OCF$_2$C$\underline{F}_2$CF$_2$O—]
δ=−123.7 ppm [4F, HOCH$_2$C≡CC$\underline{H}_2$O—CH$_2$CH(OH)CH$_2$O—CH$_2$C$\underline{F}_2$CF$_2$O—]
δ=−86.3 ppm [4F, HOCH$_2$C≡CCH$_2$O—CH$_2$CH(OH)CH$_2$O—CH$_2$CF$_2$C$\underline{F}_2$O—]
δ=−84.0 ppm [28F, —OC$\underline{F}_2$CF$_2$C$\underline{F}_2$O—]
Results of $^{19}$F-NMR showed that for Compound 2, x=7.0.
1H-NMR (solvent: none, reference substance: D$_2$O)
δ=3.1 ppm to 4.3 ppm [26H, HOC$\underline{H}_2$C≡CC$\underline{H}_2$O—C$\underline{H}_2$C$\underline{H}$(O$\underline{H}$)C$\underline{H}_2$O—C$\underline{H}_2$CF$_2$CF$_2$O—]

Example 3

Compound 3 having a structure represented by Formula (12) below was synthesized as follows:

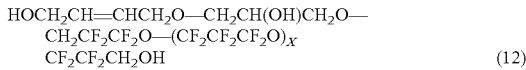

$$\begin{aligned}&\text{HOCH}_2\text{CH}{=}\text{CHCH}_2\text{O}{-}\text{CH}_2\text{CH(OH)CH}_2\text{O}{-}\\&\text{CH}_2\text{CF}_2\text{CF}_2\text{O}{-}(\text{CF}_2\text{CF}_2\text{CF}_2\text{O})_x\\&\text{CF}_2\text{CF}_2\text{CH}_2\text{OH}\end{aligned} \qquad (12)$$

Into a flask, 100 g of (Z)-but-2-ene-1,4-diol, 100 g of DMF, and 74 g of imidazole were put and stirred. Further, into the flask, 173 g of triisopropyl silyl chloride was dropped while the flask was immersed in an ice bath. After dropping of triisopropyl silyl chloride was completed, stirring was carried out at room temperature for 15 hours. Thereafter, a resulting product was washed with water and purified by silica gel chromatography, so that 98 g of Compound 3a: (Z)-4-((triisopropylsilyl)oxy)but-2-en-1-ol was obtained. Into another flask, 60 g of Compound 3a, 51 g of t-butyl alcohol, 29 g of potassium t-butoxide, and 460 g of epichlorohydrin were put and stirred in an argon atmosphere at 70° C. Then, a resulting product was purified by silica gel chromatography, so that 68 g of Compound 3b: (Z)-triisopropyl((4-(oxiran-2-ylmethoxy)but-2-ene-1-yl)oxy)silane was obtained.

Into another flask, 40 g of this Compound 3b, 200 g of perfluoropolyether (number average molecular weight 1142) having a structure represented by HO—CH$_2$CF$_2$CF$_2$O—(CF$_2$CF$_2$CF$_2$O)$_x$CF$_2$CF$_2$CH$_2$—OH, 84 g of t-butyl alcohol, and 8 g of potassium t-butoxide were put and stirred in an argon atmosphere at 70° C. for 17 hours. Then, 78 g of a brown liquid (Compound 3A) was obtained by neutralization, washing with water, and purification by silica gel chromatography. Next, 40 g of Compound 3A, and 40 g of SR solvent were put in another flask, and 20 g of 1 mol/L tetrahydrofuran solution of tetrabutylammonium fluoride was dropped into the flask. Then, stirring was carried out for 6 hours. Subsequently, 31 g of Compound 3, which was a colorless transparent liquid, was obtained by neutralization and purification by silica gel chromatography. The results of identification of Compound 3 by the NMR are as follows.

$^{19}$F-NMR (solvent: none, reference: OCF$_2$C$\underline{F}_2$CF$_2$O in the product [−129.7 ppm])
δ=−129.7 ppm, −129.6 ppm [11F, —OCF$_2$C$\underline{F}_2$CF$_2$O—]
δ=−127.4 ppm [2F, HO—CH$_2$C$\underline{F}_2$CF$_2$O—]
δ=−123.9 ppm [2F, HOCH$_2$CH=CHCH$_2$O—CH$_2$CH(OH)CH$_2$O—CH$_2$C$\underline{F}_2$CF$_2$O—]
δ=−86.3 ppm [4F, HOCH$_2$CH=CHCH$_2$O—CH$_2$CH(OH)CH$_2$O—CH$_2$CF$_2$C$\underline{F}_2$O—, HO—CH$_2$CF$_2$C$\underline{F}_2$O—]
δ=−84.0 ppm [21F, —OC$\underline{F}_2$CF$_2$C$\underline{F}_2$O—]
Results of $^{19}$F-NMR showed that for Compound 3, x=5.4.
$^1$H-NMR (solvent: none, reference substance: D$_2$O)
δ=3.0 ppm to 4.2 ppm [16H, HOC$\underline{H}_2$CH=CHC$\underline{H}_2$O—C$\underline{H}_2$C$\underline{H}$(O$\underline{H}$)C$\underline{H}_2$O—C$\underline{H}_2$CF$_2$CF$_2$O—]
δ=5.0 ppm to 5.8 ppm [2H, HOCH$_2$C$\underline{H}$=C$\underline{H}$CH$_2$O—CH$_2$CH(OH)CH$_2$O—CH$_2$CF$_2$CF$_2$O—]

Example 4

Compound 4 having a structure represented by Formula (13) below was synthesized as follows:

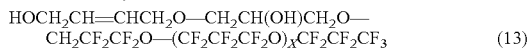

$$\begin{aligned}&\text{HOCH}_2\text{CH}{=}\text{CHCH}_2\text{O}{-}\text{CH}_2\text{CH(OH)CH}_2\text{O}{-}\\&\text{CH}_2\text{CF}_2\text{CF}_2\text{O}{-}(\text{CF}_2\text{CF}_2\text{CF}_2\text{O})_x\text{CF}_2\text{CF}_2\text{CF}_3\end{aligned} \qquad (13)$$

Compound 4 (32 g) was obtained as in Example 3 except that a compound having a structure represented by HO—CH$_2$CF$_2$CF$_2$O—(CF$_2$CF$_2$CF$_2$O)$_x$CF$_2$CF$_2$CF$_3$ was used in place of the perfluoropolyether having a structure represent by HO—CH$_2$CF$_2$CF$_2$O—(CF$_2$CF$_2$CF$_2$O)$_x$CF$_2$CF$_2$CH$_2$—OH. Compound 4 was a colorless transparent liquid. The results of identification of Compound 4 by the NMR are as follows.

$^{19}$F-NMR (solvent: none, reference: OCF$_2$C$\underline{F}_2$CF$_2$O in the product [−129.7 ppm])
δ=−130.7 ppm [2F, CF$_3$C$\underline{F}_2$CF$_2$O—]
δ=−129.7 ppm, −129.6 ppm [11F, —OCF$_2$C$\underline{F}_2$CF$_2$O—]
δ=−123.9 ppm [2F, HOCH$_2$CH=CHCH$_2$O—CH$_2$CH(OH)CH$_2$O—CH$_2$C$\underline{F}_2$CF$_2$O—]
δ=−86.5 ppm [2F, HOCH$_2$CH=CHCH$_2$O—CH$_2$CH(OH)CH$_2$O—CH$_2$CF$_2$C$\underline{F}_2$O—]
δ=−84.3 ppm to −83.6 ppm [22F, —OC$\underline{F}_2$CF$_2$C$\underline{F}_2$O—]
δ=−85.0 ppm [2F, CF$_3$CF$_2$C$\underline{F}_2$O—]
δ=−82.9 ppm [3F, C$\underline{F}_3$CF$_2$CF$_2$O—]
Results of $^{19}$F-NMR showed that for Compound 4, x=5.5.
$^1$H-NMR (solvent: none, reference substance: D$_2$O)
δ=3.0 ppm to 4.2 ppm [13H, HOC$\underline{H}_2$CH=CHC$\underline{H}_2$O—C$\underline{H}_2$C$\underline{H}$(O$\underline{H}$)C$\underline{H}_2$O—C$\underline{H}_2$CF$_2$CF$_2$O—]
δ=5.0 ppm to 5.8 ppm [2H, HOCH$_2$C$\underline{H}$=C$\underline{H}$CH$_2$O—CH$_2$CH(OH)CH$_2$O—CH$_2$CF$_2$CF$_2$O—]

Example 5

Compound 5 having a structure represented by Formula (14) below was synthesized as follows:

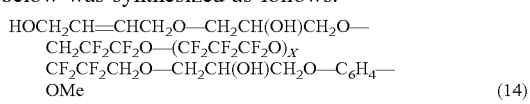

$$\begin{aligned}&\text{HOCH}_2\text{CH}{=}\text{CHCH}_2\text{O}{-}\text{CH}_2\text{CH(OH)CH}_2\text{O}{-}\\&\text{CH}_2\text{CF}_2\text{CF}_2\text{O}{-}(\text{CF}_2\text{CF}_2\text{CF}_2\text{O})_x\\&\text{CF}_2\text{CF}_2\text{CH}_2\text{O}{-}\text{CH}_2\text{CH(OH)CH}_2\text{O}{-}\text{C}_6\text{H}_4{-}\\&\text{OMe}\end{aligned} \qquad (14)$$

Into a flask, 40 g of Compound 3A (number average molecular weight 1475), 5.4 g of Glycidyl 4-methoxyphenyl ether, 18 g of t-butyl alcohol, and 0.2 g of potassium t-butoxide were put and stirred in an argon atmosphere at 70° C. for 17 hours. Then, 45 g of a brown liquid was obtained by neutralization and washing with water. Next, 45 g of the brown liquid and 45 g of SR solvent were put in another flask, and 37 g of 1 mol/L tetrahydrofuran solution of tetrabutylammonium fluoride was dropped into the flask. Then, stirring was carried out for 6 hours. Subsequently, 25 g of Compound 5, which was a colorless transparent liquid, was obtained by neutralization and purification by silica gel chromatography. The results of identification of Compound 5 by the NMR are as follows.

$^{19}$F-NMR (solvent: none, reference: OCF$_2$C$\underline{F}_2$CF$_2$O in the product [−129.7 ppm])
δ=−129.7 ppm, −129.6 ppm [12F, —OCF$_2$C$\underline{F}_2$CF$_2$O—]
δ=−123.9 ppm [4F, HOCH$_2$CH=CHCH$_2$O—CH$_2$CH(OH)CH$_2$O—CH$_2$C$\underline{F}_2$CF$_2$O—, MeO—C$_6$H$_4$—OCH$_2$CH(OH)CH$_2$—OCH$_2$C$\underline{F}_2$CF$_2$O—]
δ=−86.3 ppm [4F, HOCH$_2$CH=CHCH$_2$O—CH$_2$CH(OH)CH$_2$O—CH$_2$CF$_2$C$\underline{F}_2$O—, MeO—C$_6$H$_4$—OCH$_2$CH(OH)CH$_2$—OCH$_2$CF$_2$C$\underline{F}_2$O—]
δ=−84.0 ppm [24F, —OC$\underline{F}_2$CF$_2$C$\underline{F}_2$O—]
Results of $^{19}$F-NMR showed that for Compound 5, x=5.7.

$^{1}$H-NMR (solvent: none, reference substance: D$_2$O)
δ=3.1 ppm to 4.5 ppm [24H, HOC$\underline{H}_2$CH=CHC$\underline{H}_2$O—C$\underline{H}_2$C$\underline{H}$(OH)C$\underline{H}_2$O—C$\underline{H}_2$CF$_2$CF$_2$O—, MeO—C$_6$$\underline{H}_4$—OCH$_2$CH(OH)C$\underline{H}_2$—OC$\underline{H}_2$CF$_2$CF$_2$O—]
δ=5.0 ppm to 5.8 ppm [2H, HOCH$_2$C$\underline{H}$=C$\underline{H}$CH$_2$O—CH$_2$CH(OH)CH$_2$O—CH$_2$CF$_2$CF$_2$O—]
δ=6.9 ppm to 7.0 ppm [4H, MeO—C$_6$$\underline{H}_4$—OCH$_2$CH(OH)CH$_2$—OCH$_2$CF$_2$CF$_2$O—]

Example 6

Compound 6 having a structure represented by Formula (15) below was synthesized as follows:

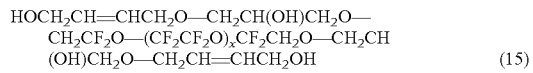

HOCH$_2$CH=CHCH$_2$O—CH$_2$CH(OH)CH$_2$O—CH$_2$CF$_2$O—(CF$_2$CF$_2$O)$_x$CF$_2$CH$_2$O—CH$_2$CH(OH)CH$_2$O—CH$_2$CH=CHCH$_2$OH  (15)

Compound 6 (60 g) was obtained as in Example 1 except that a perfluoropolyether having a structure represented by HO—CH$_2$CF$_2$O—(CF$_2$CF$_2$O)$_x$CF$_2$CH$_2$—OH was used in place of the fluoropolyether having a structure represent by HO—CH$_2$CF$_2$CF$_2$O—(CF$_2$CF$_2$CF$_2$O)$_x$CF$_2$CF$_2$CH$_2$—OH. Compound 6 was a colorless transparent liquid. The results of identification of Compound 6 by the NMR are as follows.

$^{19}$F-NMR (solvent: none, reference: OC$\underline{F}_2$CF$_2$O in the product [−90.7 ppm])
δ=−90.7 ppm [28F, —C$\underline{F}_2$C$\underline{F}_2$O—]
δ=−79.8 ppm [4F, HOCH$_2$CH=CHCH$_2$O—CH$_2$CH(OH)CH$_2$O—CH$_2$C$\underline{F}_2$O—]
Results of $^{19}$F-NMR showed that for Compound 6, x=7.0.

$^{1}$H-NMR (solvent: none, reference substance: D$_2$O)
δ=3.0 ppm to 4.5 ppm [26H, HOC$\underline{H}_2$CH=CHC$\underline{H}_2$O—C$\underline{H}_2$C$\underline{H}$(O$\underline{H}$)C$\underline{H}_2$O—C$\underline{H}_2$CF$_2$O—]
δ=5.0 ppm to 5.8 ppm [4H, HOCH$_2$C$\underline{H}$=C$\underline{H}$CH$_2$O—CH$_2$CH(OH)CH$_2$O—CH$_2$CF$_2$O—]

Comparative Examples

As Comparative Examples, the following compounds were used: Compound 7 having a hydroxy group at one terminal thereof; Compound 8 having a dihydroxypropoxy group at one terminal thereof; Compound 9 having a hydroxy group at both terminals thereof; Compound 10 having a dihydroxypropoxy group at both terminals thereof; and Compound 11 having a p-methoxybenzyl group at one terminal thereof. The following shows specific structures of Compounds 7 to 11, respectively.

Comparative Example 1: Compound 7

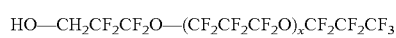

HO—CH$_2$CF$_2$CF$_2$O—(CF$_2$CF$_2$CF$_2$O)$_x$CF$_2$CF$_2$CF$_3$

For this compound, x=10.4.

Comparative Example 2: Compound 8

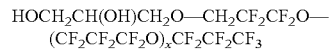

HOCH$_2$CH(OH)CH$_2$O—CH$_2$CF$_2$CF$_2$O—(CF$_2$CF$_2$CF$_2$O)$_x$CF$_2$CF$_2$CF$_3$

For this compound, x=10.5.

Comparative Example 3: Compound 9

HO—CH$_2$CF$_2$CF$_2$O—(CF$_2$CF$_2$CF$_2$O)$_x$CF$_2$CF$_2$CH$_2$—OH

For this compound, x=10.2.

Comparative Example 4: Compound 10

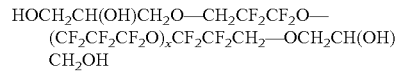

HOCH$_2$CH(OH)CH$_2$O—CH$_2$CF$_2$CF$_2$O—(CF$_2$CF$_2$CF$_2$O)$_x$CF$_2$CF$_2$CH$_2$—OCH$_2$CH(OH)CH$_2$OH

For this compound, x=6.0.

Comparative Example 5: Compound 11

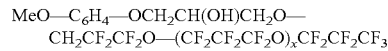

MeO—C$_6$H$_4$—OCH$_2$CH(OH)CH$_2$O—CH$_2$CF$_2$CF$_2$O—(CF$_2$CF$_2$CF$_2$O)$_x$CF$_2$CF$_2$CF$_3$

For this compound, x=10.4.

[Results of Bonding Ratio Test and Siloxane Resistance Evaluation]

Table 1 shows bonding ratios of respective lubricants.

TABLE 1

|  | Composition | Film thickness f (Å) | Film thickness b (Å) | Bonding ratio (%) |
| --- | --- | --- | --- | --- |
| Example 1 | Compound 1 | 10.18 | 8.99 | 88.3 |
| Example 2 | Compound 2 | 11.23 | 9.21 | 82.0 |
| Example 3 | Compound 3 | 12.40 | 8.42 | 67.9 |
| Example 4 | Compound 4 | 13.25 | 8.61 | 65.0 |
| Example 5 | Compound 5 | 12.20 | 8.99 | 73.7 |
| Example 6 | Compound 6 | 11.50 | 9.92 | 86.3 |
| Comparative Example 1 | Compound 7 | 10.50 | 0.02 | 0.2 |
| Comparative Example 2 | Compound 8 | 11.59 | 2.60 | 22.4 |
| Comparative Example 3 | Compound 9 | 10.10 | 0.52 | 5.1 |
| Comparative Example 4 | Compound 10 | 11.16 | 3.84 | 34.4 |
| Comparative Example 5 | Compound 11 | 11.00 | 2.09 | 19.0 |

In the cases of Compounds 1 to 6, each of which had, at one terminal thereof, at least one hydroxyalkenyl group or at least one hydroxyalkynyl group, the bonding ratio was higher than that in the cases of Compounds 7 to 11 of Comparative Examples which had neither any hydroxyalkenyl group nor any hydroxyalkynyl group. These results demonstrated that the fluoropolyether compound in accordance with an embodiment of the present invention exhibits better adsorbability on the surface of a magnetic disk than perfluoropolyether compounds having, at a terminal(s) thereof, a trifluoromethyl group, a hydroxy group, a dihydroxypropoxy group, or a methoxyphenyl group.

Table 2 shows the amount of attached D4 and the amount of lubricant adsorbed on graphite.

TABLE 2

| | Composition | Amount of attached D4 (ppm) | Amount of lubricant adsorbed on graphite (wt %) |
|---|---|---|---|
| Example 1 | Compound 1 | 2933 | 1.97 |
| Example 2 | Compound 2 | 2877 | 2.12 |
| Example 3 | Compound 3 | 3875 | 2.04 |
| Example 4 | Compound 4 | 4524 | 2.29 |
| Example 5 | Compound 5 | 3165 | 2.19 |
| Example 6 | Compound 6 | 2855 | 1.92 |
| Comparative Example 1 | Compound 7 | 12431 | 1.99 |
| Comparative Example 2 | Compound 8 | 7089 | 2.11 |
| Comparative Example 3 | Compound 9 | 9439 | 2.02 |
| Comparative Example 4 | Compound 10 | 5125 | 1.88 |
| Comparative Example 5 | Compound 11 | 5366 | 1.81 |

In the cases of Compounds 1 to 6 each of which has, at one terminal thereof, at least one hydroxyalkenyl group or at least one hydroxyalkynyl group, the amount of attached D4 was smaller than that in the cases of Compounds 7 to 11 of Comparative Examples which had neither any hydroxyalkenyl group nor any hydroxyalkynyl group. These results demonstrated that the fluoropolyether compound in accordance with an embodiment of the present invention exhibits better siloxane resistance than perfluoropolyether compounds having, at a terminal(s) thereof, a trifluoromethyl group, a hydroxy group, a dihydroxypropoxy group, or a methoxyphenyl group. The siloxane resistance evaluation is evaluation of how easily impurities attach to a protective layer, by measuring the amount of attached siloxane which is a typical contaminant in a production process of a magnetic disk. That is, when a lubricant that contains any one of the compounds synthesized in Examples 1 to 6 is used, the tendency of impurity contamination of the protective layer, which underlies the lubricant layer, is smaller as compared to when any one of the compounds synthesized in Comparative Examples 1 to 5 is used.

INDUSTRIAL APPLICABILITY

A fluoropolyether compound in accordance with an aspect of the present invention prevents or reduces attachment of impurities on a protective layer, even when placed on the protective layer so as to form a thin lubricant layer. The present invention is therefore suitable for use as a lubricant for a magnetic disk.

REFERENCE SIGNS LIST 1 magnetic disk
2 lubricant layer
3 protective film layer (protective layer)
4 recording layer
5 lower layer
6 soft magnetic lower layer
7 adhesive layer
8 non-magnetic substrate

The invention claimed is:

1. A fluoropolyether compound having a structure represented by Formula (1) below:

$$R^1-R^2-R^3 \quad (1)$$

where:
$R^2$ represents a perfluoropolyether;
$R^1$ and $R^3$ each independently represent an organic group having, at a terminal thereof, a hydroxyl group, a halogenated alkyl group, an alkoxy group, a carboxy group, an amino group, an ester group, an amide group, or an aryl group; and
at least one of $R^1$ and $R^3$ contains a hydroxyalkenyl group which has a hydroxyl group at a terminal thereof, or a hydroxyalkynyl group which has a hydroxyl group at a terminal thereof.

2. The fluoropolyether compound as set forth in claim 1, wherein:
in a case where at least one of $R^1$ and $R^3$ contains the hydroxyalkenyl group which has a hydroxyl group at a terminal thereof, the hydroxyalkenyl group has a structure represented by Formula (2) below; and
in a case where at least one of $R^1$ and $R^3$ contains the hydroxyalkynyl group which has a hydroxyl group at a terminal thereof, the hydroxyalkynyl group has a structure represented by Formula (3) below:

$$-(CH_2)_a-CH=CH-(CH_2)_b-OH \quad (2)$$

where a and b are each a real number of 1 to 4, and $$-(CH_2)_c-C\equiv C-(CH_2)_d-OH \quad (3)$$

where c and d are each a real number of 1 to 4.

3. The fluoropolyether compound as set in claim 1, wherein R2 has a structure represented by Formula (4) below:

$$-(CF_2)_x(CF(CF_3))_yO(CF_2O)_z(CF_2CF_2O)_l(CF_2CF_2CF_2O)_m(CF_2CF_2CF_2CF_2O)_n(CF(CF_3)CF_2O)_o-(CF(CF_3))_y(CF_2)_x- \quad (4)$$

where
x is a real number of 0 to 3,
y is a real number of 0 to 1, and
z, l, m, n, and o are each a real number of 0 to 15.

4. The fluoropolyether compound as set forth in claim 1, wherein:
in a case where at least one of $R^1$ and $R^3$ contains the hydroxyalkenyl group which has a hydroxyl group at a terminal thereof, the at least one of $R^1$ and $R^3$ has a structure represented by Formula (5) below; and
in a case where at least one of $R^1$ and $R^3$ contains the hydroxyalkynyl group which has a hydroxyl group at a terminal thereof, the at least one of $R^1$ and $R^3$ has a structure represented by Formula (6) below:

$$-CH_2OCH_2CH(OH)CH_2O-(CH_2)_p-CH=CH-(CH_2)_q-OH \quad (5)$$

where p and q are each a real number of 1 to 4, and $$-CH_2OCH_2CH(OH)CH_2O-(CH_2)_r-C\equiv C-(CH_2)_s-OH \quad (6)$$

where r and s are each a real number of 1 to 4.

5. A fluoropolyether compound having a structure represented by Formula (1') below:

$$R^{1'}-OCH_2CH(OH)CH_2OCH_2-R^2-R^3 \quad (1')$$

where:
(i) $R^{1'}$ contains
a hydroxyalkenyl group having a structure represented by Formula (2) below, or
a hydroxyalkynyl group having a structure represented by Formula (3) below:

$$-(CH_2)_a-CH=CH-(CH_2)_b-OH \quad (2)$$

where a and b are each a real number of 1 to 4, or $$-(CH_2)_c-C\equiv C-(CH_2)_d-OH \quad (3)$$

where c and d are each a real number of 1 to 4;

(ii) $R^2$ has a structure represented by Formula (4) below:

$$-(CF_2)_x(CF(CF_3))_yO(CF_2O)_z(CF_2CF_2O)_l(CF_2CF_2CF_2O)_m(CF_2CF_2CF_2CF_2O)_n(CF(CF_3)CF_2O)_o-(CF(CF_3))_y(CF_2)_xO- \quad (4)$$

where
x is a real number of 0 to 3,
y is a real number of 0 to 1, and
z, l, m, n, and o are each a real number of 0 to 15; and
(iii) $R^3$ contains
a hydroxyalkenyl group having a structure represented by Formula (5) below,
a hydroxyalkynyl group having a structure represented by Formula (6) below, or
a structure represented by any of Formulae (7) to (9) below:

$$-CH_2OCH_2CH(OH)CH_2O-(CH_2)_p-CH=CH-(CH_2)_q-OH \quad (5)$$

where p and q are each a real number of 1 to 4, $$-CH_2OCH_2CH(OH)CH_2O-(CH_2)_r-C\equiv C-(CH_2)_s-OH \quad (6)$$

where r and s are each a real number of 1 to 4, $$-(CH_2CH(OH)CH_2O)_t-H \quad (7)$$

where t is a real number of 0 to 5, $$-(CF_2)_uCF_3 \quad (8)$$

where u is a real number of 0 to 3, and $$-CH_2OCH_2CH(OH)CH_2O-C_6H_4-OMe \quad (9).$$

6. A fluoropolyether compound having a structure represented by any Formulae (10) to (15) below:

$$HOCH_2CH=CHCH_2O-CH_2CH(OH)CH_2O-CH_2CF_2CF_2O-(CF_2CF_2CF_2O)_X CF_2CF_2CH_2O-CH_2CH(OH)CH_2O-CH_2CH=CHCH_2OH \quad (10)$$

$$HOCH_2C\equiv CCH_2O-CH_2CH(OH)CH_2O-CH_2CF_2CF_2O-(CF_2CF_2CF_2O)_X CF_2CF_2CH_2O-CH_2CH(OH)CH_2O-CH_2C\equiv CCH_2OH \quad (11)$$

$$HOCH_2CH=CHCH_2O-CH_2CH(OH)CH_2O-CH_2CF_2CF_2O-(CF_2CF_2CF_2O)_X CF_2CF_2CH_2OH \quad (12)$$

$$HOCH_2CH=CHCH_2O-CH_2CH(OH)CH_2O-CH_2CF_2CF_2O-(CF_2CF_2CF_2O)_X CF_2CF_2CF_3 \quad (13)$$

$$HOCH_2CH=CHCH_2O-CH_2CH(OH)CH_2O-CH_2CF_2CF_2O-(CF_2CF_2CF_2O)_X CF_2CF_2CH_2O-CH_2CH(OH)CH_2O-C_6H_4-OMe \quad (14)$$

$$HOCH_2CH=CHCH_2O-CH_2CH(OH)CH_2O-CH_2CF_2O-(CF_2CF_2O)_X CF_2CH_2O-CH_2CH(OH)CH_2O-CH_2CH=CHCH_2OH \quad (15)$$

wherein x is a real number of 1 to 15.

7. A lubricant comprising a fluoropolyether compound recited in claim 1.

8. A magnetic disk comprising:
a recording layer,
a protective layer disposed on the recording layer; and
a lubricant layer disposed on the protective layer,
the lubricant layer containing a lubricant in claim 7.

9. A method of producing a magnetic disk that includes a recording layer, a protective layer disposed on the recording layer, and a lubricant layer disposed on the protective layer,
the method comprising the step of forming the lubricant layer by placing a lubricant recited in claim 7 on an exposed surface of the protective layer of a stack of the recording layer and the protective layer.

10. A lubricant comprising a Fluoropolyether compound recited in claim 5.

11. A magnetic disk comprising:
a recording layer;
a protective layer disposed on the recording layer; and
a lubricant layer disposed on the protective layer,
the lubricant layer containing a lubricant recited in claim 10.

12. A method of producing a magnetic disk that includes a recording layer, a protective layer disposed on the recording layer, and a lubricant layer disposed on the protective layer,
the method comprising the step of forming the lubricant layer by placing a lubricant recited in claim 10 on an exposed surface of the protective layer of a stack of the recording layer and the protective layer.

13. A lubricant comprising a Fluoropolyether compound recited in claim 6.

14. A magnetic disk comprising:
a recording layer;
a protective layer disposed on the recording layer; and
a lubricant layer disposed on the protective layer,
the lubricant layer containing a lubricant recited in claim 13.

15. A method of producing a magnetic disk that includes a recording layer, a protective layer disposed on the recording layer, and a lubricant layer disposed on the protective layer,
the method comprising the step of forming the lubricant layer by placing a lubricant recited in claim 13 on an exposed surface of the protective layer of a stack of the recording layer and the protective layer.

* * * * *